United States Patent
Moor et al.

(10) Patent No.: US 8,507,759 B2
(45) Date of Patent: Aug. 13, 2013

(54) LETTUCE VARIETY 79-88 RZ

(75) Inventors: Cornelis Marinus Moor, Monster (NL); Egbert Carolus Johannes Smits, Zevenbergen (NL)

(73) Assignee: Rijk Zwaan Zaadteelt en Zaadhandel B.V., De Lier (NL)

( * ) Notice: Subject to any disclaimer, the term of this patent is extended or adjusted under 35 U.S.C. 154(b) by 625 days.

(21) Appl. No.: 12/487,795

(22) Filed: Jun. 19, 2009

(65) Prior Publication Data
US 2010/0325749 A1 Dec. 23, 2010

(51) Int. Cl.
*A01H 1/00* (2006.01)
*A01H 4/00* (2006.01)
*A01H 5/00* (2006.01)
*A01H 5/10* (2006.01)
*C12N 15/82* (2006.01)

(52) U.S. Cl.
USPC ........... 800/305; 435/410; 435/419; 800/260; 800/278; 800/298

(58) Field of Classification Search
None
See application file for complete search history.

(56) References Cited

U.S. PATENT DOCUMENTS 7,504,562 B2 * 3/2009 Schut et al. ............... 800/305

* cited by examiner

*Primary Examiner* — Eileen B O Hara
(74) *Attorney, Agent, or Firm* — Vedder Price P.C.; Thomas J. Kowalski; Deborah L. Lu

(57) ABSTRACT

The present invention relates to a lettuce cultivar having resistance to downy mildew (*Bremia lactucae* Regel), currant-lettuce aphid (*Nasonovia ribis-nigri*) and lettuce mosaic virus (LMV), and which has green, deeply-incised, nicely-frilled leaves. The invention further relates to methods for producing the lettuce cultivar, represented by lettuce variety 79-88 RZ, representative seed having been deposited under NCIMB Accession No. 41615.

20 Claims, 1 Drawing Sheet
(1 of 1 Drawing Sheet(s) Filed in Color)

LETTUCE VARIETY 79-88 RZ

INCORPORATION BY REFERENCE

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a new lettuce (*Lactuca sativa*) variety which exhibits resistance against downy mildew (*Bremia lactucae*), currant-lettuce aphid (*Nasonovia ribis-nigri*) and lettuce mosaic virus (LMV) as well as green, crisp, deeply-incised, nicely-frilled shaped leaves.

BACKGROUND OF THE INVENTION

All cultivated forms of lettuce belong to the highly polymorphic species, *Lactuca sativa*, which is grown for its edible head and leaves. As a crop, lettuces are grown commercially wherever environmental conditions permit the production of an economically viable yield.

*Lactuca sativa* is in the Cichoreae tribe of the Asteraceae (Compositae) family. Lettuce is related to chicory, sunflower, aster, scorzonera, dandelion, artichoke and chrysanthemum. *Sativa* is one of about 300 species in the genus *Lactuca*.

Lettuce cultivars are susceptible to a number of pests and diseases such as downy mildew (*Bremia lactucae*), currant-lettuce aphid (*Nasonovia ribis-nigri*) and lettuce mosaic virus (LMV). These diseases result in millions of dollars of lost lettuce crop throughout the world every year.

Downy mildew (*Bremia lactucae*) is highly destructive of lettuce grown at relatively low temperature and high humidity. Downy mildew is caused by a fungus, *Bremia lactucae*, which can be one of the following strains: NL1, NL2, NL4, NL5, NL6, NL7, NL10, NL12, NL13, NL14, NL15, NL16, Bl:17, Bl:18, Bl:21, Bl:22, Bl:23, Bl:24, Bl:25, Bl:26, (Van Ettekoven, K. et al., "Identification and denomination of 'new' races of *Bremia lactucae*," In: Lebeda, A. and Kristkova, E (eds.), Eucarpia Leafy Vegetables, 1999, Palacky University, Olomouc, Czech Republic, pp. 171-175; Van der Arend et al. "Identification and denomination of "new" races of *Bremia lactucae* in Europe by IBEB until 2002." In: Van Hintum, Th et al. (eds.), Eucarpia Leafy Vegetables Conference 2003, Centre for Genetic Resources, Wageningen, The Netherlands, p. 151), Ca-V, Ca-VI, Ca-VII, Ca-VIII (Michelmore R. & Ochoa. O. "Breeding Crisphead Lettuce." In: California Lettuce Research Board, Annual Report 2005-2006, 2006, Salinas, California, pp. 55-68).

Downy mildew causes pale, angular, yellow areas bounded by veins on the upper leaf surfaces. Sporulation occurs on the opposite surface of the leaves. The lesions eventually turn brown, and they may enlarge and coalesce. These symptoms typically occur first on the lower leaves of the lettuce, but under ideal conditions may move into the upper leaves of the head. When the fungus progresses to this degree, the head cannot be harvested. Less severe damage requires the removal of more leaves than usual, especially when the lettuce reaches its final destination.

Lettuce mosaic virus (LMV) mainly infects lettuce seeds, which is the primary way that the virus is introduced to lettuce in the fields, but also can infect numerous crops and weeds, thereby creating reservoirs of the virus. LMV also can be vectored by aphids, which spread the virus within a lettuce field and introduce it into lettuce fields from infected weeds and crops outside the field.

Of the various species of aphids that feed on lettuce, the currant-lettuce aphid (*Nasonovia ribis-nigri*) is the most destructive species because it feeds both on the leaves of the lettuce as well as deep in the heart of the lettuce, making it difficult to control with conventional insecticides. The lettuce aphid feeds by sucking sap from the lettuce leaves. Although direct damage to the lettuce may be limited, its infestation has serious consequences because the presence of aphids makes lettuce unacceptable to consumers.

Symptoms of lettuce mosaic virus vary greatly. Leaves of plants that are infected at a young stage are stunted, deformed, and (in some varieties) show a mosaic or mottling pattern. Such plants rarely grow to full size; head lettuce varieties infected early fail to form heads. Plants that are infected later in the growth cycle show a different set of symptoms. These plants may reach full size, but the older outer leaves turn yellow, twisted, and otherwise are deformed. On head lettuce, the wrapper leaves often will curve back away from the head and developing heads may be deformed. In some cases brown, necrotic flecks occur on the wrapper leaves.

Although several known lettuce cultivars exhibit resistance against disease, irrespective of lettuce type, many lettuce cultivars affected produce large leaves that, when cut to smaller size pieces generally result in a lot of cut surface resulting in a diminished shelf life with respect to wound-induced discolouration of these cut surfaces. Light green or 'blond' varieties have the additional disadvantage that the leaf pieces are considered pale and therefore visually non-fresh. These are distinct disadvantages for processing regular lettuce types.

Although several known lettuce cultivars can be harvested mechanically at young plant, i.e. babyleaf stage, no pest and disease resistant lettuce cultivars exist that can be harvested mechanically at mature stage and still provide leaf pieces that are of small, directly edible size and have an attractive green and non-pale colour. Mechanical harvesting saves labour cost and improves labour conditions in comparison with commonly applied hand-harvesting methods.

There exists a need, therefore, for an mechanically harvestable lettuce variety which exhibits a combination of resistance against downy mildew (*Bremia lactucae*), currant-lettuce aphid (*Nasonovia ribisnigri*) and lettuce mosaic virus (LMV).

Citation or identification of any document in this application is not an admission that such document is available as prior art to the present invention.

SUMMARY OF THE INVENTION

The present invention provides a new type of lettuce (*Lactuca sativa*) variety, designated 79-88 RZ. Lettuce cultivar 79-88 RZ exhibits a combination of resistance to downy mildew (*Bremia lactucae* Regel), currant-lettuce aphid (*Nasonovia ribis-nigri*) and lettuce mosaic virus (LMV) as well as green, deeply-incised, nicely-frilled leaves. Seeds of lettuce cultivar 79-88 RZ have been deposited under the Budapest Treaty with the National Collections of Industrial, Marine and Food Bacteria (NCIMB) in Bucksburn, Aberdeen AB21

9YA, Scotland, UK and have been assigned NCIMB Accession No. 41615. Deposited seeds will be irrevocably and without restriction or condition released to the public during the term of any patent issued from this application.

The present invention also provides parts of the plant of lettuce cultivar 79-88 RZ that are suitable for sexual reproduction, which include, without limitation, microspores, pollen, ovaries, ovules, embryo sacs or egg cells.

The present invention further provides parts of the plant of lettuce cultivar 79-88 RZ that are suitable for vegetative reproduction, which include, without limitation, cuttings, roots, stems, cells or protoplasts, leaves, meristems or buds.

The present invention still further provides a tissue culture from lettuce cultivar 79-88 RZ in which the tissue culture is derived from a tissue such as, for example and without limitation, leaves, pollen, embryos, cotyledon, hypocotyls, meristematic cells, roots, root tips, anthers, flowers, seeds or stems.

The present invention also provides a plant grown from the seeds, regenerated from the above-described plant parts, or regenerated from the above-described tissue culture, having all of the morphological and physiological characteristics of lettuce cultivar 79-88 RZ.

The present invention further provides progeny of lettuce cultivar 79-88 RZ produced by sexual or vegetative reproduction, grown from seeds, regenerated from the above-described plant parts, or regenerated from the above-described tissue culture of the lettuce cultivar or a progeny plant thereof, in which the regenerated plant has all of the morphological and physiological characteristics of lettuce cultivar 79-88 RZ.

The present invention still further provides a method of producing a hybrid lettuce seed comprised of crossing a first parent lettuce plant with a second parent lettuce plant and harvesting the resultant hybrid lettuce seed, in which the first parent lettuce plant or the second parent lettuce plant is the lettuce cultivar 79-88 RZ.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

The Deposit with the National Collections of Industrial, Marine and Food Bacteria (NCIMB) in Bucksburn, Aberdeen AB21 9YA, Scotland, UK, under deposit accession number 41615 were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings, in which:

FIG. 1 is a photograph of lettuce variety 79-88 RZ.

DETAILED DESCRIPTION

The present invention provides a new type of lettuce (*Lactuca sativa*) variety, designated 79-88 RZ. Lettuce cultivar 79-88 RZ exhibits a combination of resistance to downy mildew (*Bremia lactucae*), currant-lettuce aphid (*Nasonovia ribis-nigri*) and lettuce mosaic virus (LMV) as well as green, deeply-incised, nicely-frilled leaves. Seeds of lettuce cultivar 79-88 RZ have been deposited under the terms of the Budapest Treaty with the National Collections of Industrial, Marine and Food Bacteria (NCIMB) in Bucksburn, Aberdeen AB21 9YA, Scotland, UK and have been assigned NCIMB Accession No. 41615. Deposited seeds will be irrevocably and without restriction or condition released to the public during the term of any patent issued from this application.

As used herein, resistance to *Bremia lactucae* may refer to the capacity of a plant to resist infection by each of the aforementioned strains of the *Bremia lactucae* in all stages between the seedling stage and the harvestable plant stage. Resistance typically is tested by two interchangeable methods, as described by Bonnier, F. J. M. et al. (Euphytica, 61(3):203-211, 1992). One method involves inoculating 7-day old seedlings and observing sporulation 10 to 14 days later. The other method involves inoculating leaf discs with a diameter of approximately 18 mm obtained from a non-senescent, fully grown true leaf and observing sporulation 10 days later.

As used herein, resistance against *Nasonovia ribis-nigri* (Mosley), or currant-lettuce aphid, may refer to the plant characteristic which results in a non-feeding response of the aphid on the leaves of the plant in all stages between 5 true-leaf stage and harvestable plant stage (U.S. Pat. No. 5,977, 443 to Jansen, J. P. A., "Aphid Resistance in Composites," p. 12, 1999; incorporated herein by reference). Resistance is tested by spreading at least ten aphids of biotype Nr:0 on a plant in a plant stage between 5 true leaves and harvestable stage, and observing the density of the aphid population on the plant as well as the growth reduction after 14 days in a greenhouse, with temperature settings of 23 degrees Celsius in daytime and 21 degrees Celsius at night. Daylength is kept at 18 hours by assimilation lights.

As used herein, resistance against lettuce mosaic virus (LMV) may refer to the ability of the plant to grow normally after LMV infection and to inhibit the virus transmission via seed. Resistance is tested by mechanical inoculation of young plants in a climate cell or a greenhouse, as described by Pink, D. A. C. et al. (Plant Pathology, 41(1):5-12, 1992), incorporated herein by reference. Inoculated resistant plants grow just as well as uninoculated plants and show no chlorosis or mosaic symptoms. The LMV isolate which is used for testing is Ls-1 (International Union for the Protection of New Varieties of Plants [UPOV]), Guidelines for the conduct of tests for distinctness, uniformity and stability; lettuce (*Lactuca sativa L.*), 2002, p. 35; incorporated herein by reference).

As used herein, an acceptable product for consumers and/or the lettuce processing industry is defined as the absence of tipburn, a high number of relatively uniform-sized, green, three-dimensional, i.e. non-flat, lettuce leaf pieces with small-sized cut surfaces, which have preferably been obtained by mechanical harvesting.

In an embodiment of the present invention, there also is provided parts of the plant of lettuce cultivar 79-88 RZ that are suitable for sexual reproduction, which include, without limitation, microspores, pollen, ovaries, ovules, embryo sacs or egg cells.

In another embodiment, there is provided parts of the plant of lettuce cultivar 79-88 RZ that are suitable for vegetative reproduction, which include, without limitation, cuttings, roots, stems, cells, protoplasts, leaves, meristems or buds.

In a further embodiment, there is provided a tissue culture from lettuce cultivar 79-88 RZ in which the tissue culture is derived from a tissue such as, for example and without limitation, leaves, pollen, embryos, cotyledon, hypocotyls, meristematic cells, roots, root tips, anthers, flowers, seeds or stems.

In still a further embodiment, there is provided a plant grown from the seeds, regenerated from the above-described plant parts, or regenerated from the above-described tissue culture, having all of the morphological and physiological characteristics of lettuce cultivar 79-88 RZ.

In still another embodiment, there is provided progeny of lettuce cultivar 79-88 RZ produced by sexual or vegetative reproduction, grown from seeds, regenerated from the above-described plant parts, or regenerated from the above-described tissue culture of the lettuce cultivar or a progeny plant thereof, in which the regenerated plant has all of the morphological and physiological characteristics of lettuce cultivar 79-88 RZ. Progeny of the lettuce cultivar 79-88 RZ can be modified in one or more other characteristics, in which the modification is a result of, for example and without limitation, mutagenesis or transformation with a transgene.

In still a further embodiment, there is provided a method of producing a hybrid lettuce seed comprised of crossing a first parent lettuce plant with a second parent lettuce plant and harvesting the resultant hybrid lettuce seed, in which the first parent lettuce plant or the second parent lettuce plant is the lettuce cultivar 79-88 RZ.

In a preferred embodiment, the specific type of breeding method employed for developing a lettuce cultivar may be pedigree selection, where both single plant selection and mass selection practices are employed. Pedigree selection, also known as the "Vilmorin system of selection," is described in Fehr, W., Principles of Cultivar Development, Volume I, MacMillan Publishing Co., which is hereby incorporated by reference.

In general, selection is first practiced among $F_2$ plants. In the next season, the most desirable $F_3$ lines are first identified, then desirable $F_3$ plants within each line are selected. The following season and in all subsequent generations of inbreeding, the most desirable families are identified first, then desirable lines within the selected families are chosen, and finally desirable plants within selected lines are harvested individually. A family may refer to lines that were derived from plants selected from the same progeny from the preceding generation.

Using this pedigree method, two parents may be crossed using an emasculated female and a pollen donor (male) to produce $F_1$ offspring. Lettuce is an obligate self-pollination species, which means that pollen is shed before stigma emergence, assuring 100% self-fertilization. Therefore, in order to optimize crossing, a method of misting may be used to wash the pollen off prior to fertilization to assure crossing or hybridization.

Parental varieties may be selected from commercial varieties that individually exhibit one or more desired phenotypes. Additionally, any breeding method involving selection of plants for the desired phenotype may be used in the method of the present invention. The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

The present invention will now be further described by way of the following non-limiting example, which is intended to be illustrative only, as numerous modifications and variations therein will be apparent to those skilled in the art.

EXAMPLE 1

Development and Characteristics of Lettuce Cultivar 79-88 RZ

The breeding history of the lettuce cultivar of the present invention was as follows: in 2002 a cross was made in Fijnaart, the Netherlands, between mother plant "02S.4104", selected from a Rijk Zwaan breeding line of fast-bolting, light green, indoor lettuce with deeply incised leaves, and father plant "02P.32899", selected from a Rijk Zwaan breeding line of slow-bolting, light to medium green, outdoor lettuce of the lollo bionda type. Lollo bionda type lettuce has mature leaves without leaf incisions and with shallowly dentate, strongly undulated leaf margins. Plant "02S.4104" was *Bremia*-resistant, *Nasonovia*-susceptible and LMV-susceptible. Plant "02P.32899" was *Bremia*-resistant, *Nasonovia*-resistant and LMV-resistant. The F1-seed designated "02P.97395" was directly sown and brought to flowering in a glasshouse in Fijnaart, the Netherlands, to produce $F_2$-seed, designated "03P.89432", which was sown in July 2003 in a early autumn outdoor trial in Fijnaart, The Netherlands.

In September, 2003, an $F_2$-plant was selected for its slow bolting phenotype, absence of tipburn, and having deeply incised leaves, *Nasonovia*-and LMV-resistance. The $F_2$-plant produced $F_3$-seed, designated "04P.80194", which was sown in March, 2004, in a spring outdoor trial in Fijnaart, The Netherlands.

In June, 2004, an $F_3$-plant was selected for its slow bolting phenotype, absence of tipburn and having deeply incised leaves and *Nasonovia*-resistance. The $F_3$-plant produced $F_4$-seed, designated "05P.75204", which was sown in June, 2005, in a summer outdoor trial in Fijnaart, The Netherlands.

In August, 2005, an $F_4$-plant was selected for its slow bolting phenotype, absence of tipburn and having deeply incised leaves and *Nasonovia*-resistance. The $F_4$-plant produced $F_5$-seed, designated "06P.81075", which was sown in July, 2006, in a summer outdoor trial in Aramon, France.

In September, 2006, an $F_5$-plant was selected for its slow bolting phenotype, absence of tipburn and having medium green, deeply incised leaves and *Nasonovia*-resistance. The $F_5$-plant produced $F_6$-seed, designated "07P.75070", which was sown in March, 2007, in a spring outdoor trial in Fijnaart, the Netherlands.

In May, 2007, an $F_6$-plant was selected for its slow bolting phenotype, absence of tipburn and having medium green, deeply incised leaves and *Nasonovia*-resistance. The $F_6$-plant produced $F_7$-seed, designated "07P.90795", which was uniformly resistant against downy mildew (*Bremia lactucae*), currant-lettuce aphid (*Nasonovia ribis-nigri*), and lettuce mosaic virus (LMV). Based on several confidential trials performed in 2008, the $F_7$-seed also was uniform for leaf type, field performance, bolting and sensitivity for tipburn.

In the autumn of 2007, the $F_7$-seed was used to sow a multiplication in Daylesford, Australia. The progeny of this multiplication showed phenotypical uniformity during seed production and seed was harvested for further trials. In several confidential trials conducted in 2008, the multiplied seed, designated by the introduction number 79-88 RZ, displayed a harvested product which had the characteristics acceptable by the lettuce processing industry and/or consumers. The obtained cultivar was given the name "Expedition".

In the Tables that follow, the traits and characteristics of the *Lactuca sativa* L. var. longifolia Lam cutting/leaf lettuce plant having the designation 79-88 RZ are given compared to the most similar variety, referred to as "Virgile" and a standard regional check variety, referred to as "Grand Rapids" Observations were made in a trial in Wageningen, the Netherlands in 2008. Planting date was Apr. 10, 2008.

In Table 1, the seed color, cotyledon shape and characteristic of the fourth leaf of "79-88" is compared with "Virgile" and "Grand Rapids". RHS=Royal Horticultural Society Colour Chart, 5$^{th}$ Edition, London, UK.

TABLE 1

| Character | "79-88" | "Virgile" | "Grand Rapids" |
|---|---|---|---|
| Plant Type | cutting/leaf | cutting/leaf | cutting/leaf |
| Seed color | White (Silver Gray) | White (Silver Gray) | Black (Grey Brown) |
| Cotyledon Shape | Intermediate | Broad | Intermediate |
| Cotyledon Shape of the Fourth Leaf | Spatulate | Spatulate | Spatulate |
| Length/Width Index of the Fourth Leaf | 15 L/W × 10 | 13 L/W × 10 | 14 L/W × 10 |
| Fourth Leaf Apical Margin | Coarsely Dentate | Coarsely Dentate | Entire |
| Fourth Leaf Basal Margin | Incised | Incised | Coarsely Dentate |
| Undulation | Slight to Medium | Slight | Medium |
| Green Color | Medium Green (RHS 144A) | Light Green n(RHS 144B) | Light Green (RHS 144B) |
| Anthocyanin Distribution | Absent | Absent | Absent |
| Cotyledon Rolling of Fourth Leaf Stage | Present | Present | Present |
| Cotyledon Cupping of Fourth Leaf Stage | Slight | Slight | Uncupped |
| Cotyledon Reflexing of Fourth Leaf Stage | Apical Margin | Apical Margin | Apical and Lateral Margins |

In Table 2, the mature leaf and head characteristics of "79-88" is compared with "Virgile" and "Grand Rapids".

TABLE 2

| Character | "79-88" | "Virgile" | "Grand Rapids" |
|---|---|---|---|
| Maturity (Earliness of Harvest-Mature Head formation (Spring Season)) | 88 days | 88 days | 92 days |
| Green Color | Medium Green (RHS 144A) | Yellowish Light Green (RHS 144B) | Light Green (RHS 144B) |
| Margin Incision Depth | Moderate to Deep | Moderate to Deep | Absent/Shallow to Moderate |
| Margin Indentation | Shallow Dentate | Shallow Dentate | Shallowly Dentate |
| Undulations of the Apical Margin | Strong | Strong | Moderate to Strong |
| Anthocyanin Distribution | Absent | Absent | Absent |
| Leaf Size | Medium | Medium | Large |
| Leaf Glossiness | Dull | Dull | Moderate |
| Leaf Blistering | Absent/Slight | Absent/Slight | Moderate |
| Leaf Thickness | Intermediate to Thin | Thin | Intermediate |
| Trichomes | Absent | Absent | Absent |
| Spread of Frame Leaves | 37 cm | 34 cm | 37 cm |
| Head Diameter | 37 cm | 34 cm | 37 cm |
| Head Shape | Non-heading | Non-heading | Non-heading |
| Head Size Class | Medium | Medium | Medium |
| Head Weight | 1255 g | 816 g | 1225 g |
| Head Firmness | Loose | Loose | Moderate |

In Table 3, the characteristics of the butt, core and bolter plant "79-88" is compared with "Virgile" and "Grand Rapids".

TABLE 3

| Character | "79-88" | "Virgile" | "Grand Rapids" |
|---|---|---|---|
| Butt Shape | Rounded | Rounded | Rounded |
| Butt Midrib | Moderately Raised | Moderately to Prominently Raised | Prominently Raised |
| Core Diameter at Base of Head | 33 mm | 33 mm | 42 mm |
| Ratio of Head Diameter/Core Diameter | 11.0 | 10.3 | 8.9 |
| Core Height From Base of Head to Apex | 64 mm | 49 mm | 83 mm |
| Number of days from first water date to seed stalk emergence | 121 | 136 | 114 |
| Bolting Class | Very Slow | Very Slow | Slow |
| Height of Mature Seed Stalk | 95 cm | 60 cm | 120 cm |
| Spread of Bolter Plant | 21 cm | 32 cm | 42 cm |
| Bolter Leaves | Curved | Curved | Curved |
| Bolter Margin | Dentate | Dentate | Dentate |
| Bolter Color | Medium Green (RHS 144A) | Light Green (RHS 144B) | Light Green (RHS 144B) |
| Bolter Terminal Fluorescence | Absent | Present | Absent |
| Lateral Shoots of Bolter | Present | Present | Present |
| Basal Side Shoots of Bolter | Present | Absent | Present |

The invention is further described by the following numbered paragraphs:

1. A lettuce plant designated "79-88 RZ", representative seed of which having been deposited under NCIMB Accession No. 41615, wherein said plant has resistance to downy mildew (*Bremia lactucae* Regal), currant-lettuce aphid (*Nasonovia ribis-nigri*) and lettuce mosaic virus (LMV).

2. A seed of the plant of paragraph 1.

3. A part of the plant of paragraph 1, wherein said part of the plant is suitable for sexual reproduction.

4. The part of the plant of paragraph 3, said part selected from the group consisting of microspores, pollen, ovaries, ovules, embryo sacs and egg cells.

5. A part of the plant of paragraph 1, wherein said part of the plant is suitable for vegetative reproduction.

6. The part of the plant of paragraph 5, said part selected from the group consisting of cuttings, roots, stems, cells and protoplasts.

7. A tissue culture of regenerable cells or protoplasts from the lettuce plant of paragraph 1.

8. The tissue culture of paragraph 7, wherein said cells or protoplasts of the tissue culture which are derived from a tissue selected from the group consisting of leaves, pollen, embryos, cotyledon, hypocotyls, meristematic cells, roots, root tips, anthers, flowers, seeds and stems.

9. A plant that has all of the morphological and physiological characteristics of lettuce cultivar 79-88 RZ, representative seed of which having been deposited under NCIMB Accession No. 41615, said plant grown from the seed of paragraph 2.

10. A plant that has all of the morphological and physiological characteristics of lettuce cultivar 79-88 RZ, representative seed of which having been deposited under NCIMB Accession No. 41615, said plant regenerated from the part of the plant of paragraph 3.

11. A plant that has all of the morphological and physiological characteristics of lettuce cultivar 79-88 RZ, representative seed of which having been deposited under NCIMB Accession No. 41615, said plant regenerated from the tissue culture of paragraph 7.

12. A progeny of the lettuce plant of paragraph 1.

13. The progeny of paragraph 12, wherein said progeny is produced by sexual or vegetative reproduction of said lettuce plant or a progeny plant thereof, and wherein the regenerated plant has all of the morphological and physiological characteristics of lettuce cultivar 79-88 RZ, representative seed of which having been deposited under NCIMB Accession No. 41615.

14. A progeny of the lettuce plant of paragraph 9.

15. A progeny of the lettuce plant of paragraph 10.

16. A progeny of the lettuce plant of paragraph 11.

17. A progeny of the lettuce plant of paragraph 1, wherein the plant has the resistance to downy mildew (*Bremia lactucae* Regal), currant-lettuce aphid (*Nasonovia ribis-nigri*) and lettuce mosaic virus (LMV) as found in lettuce cultivar 79-88 RZ, representative seed of which having been deposited under NCIMB Accession No. 41615, and is modified in one or more other characteristics.

18. The progeny of paragraph 17, wherein the modification is effected by mutagenesis.

19. The progeny of paragraph 17, wherein the modification is effected by transformation with a transgene.

20. A method of producing a hybrid lettuce seed, comprising:
crossing a first parent lettuce plant with a second parent lettuce plant and harvesting the resultant hybrid lettuce seed, wherein said first parent lettuce plant or said second parent lettuce plant is the lettuce plant of paragraph 1.

21. A method of producing a lettuce cultivar having resistance to downy mildew (*Bremia lactucae* Regal), currant-lettuce aphid (*Nasonovia ribis-nigri*) and lettuce mosaic virus (LMV), comprising:
(a) crossing a mother lettuce plant with a father lettuce plant to produce a hybrid seed;

(b) growing said hybrid seed to produce a hybrid plant;
(c) selfing said hybrid seed to produce $F_2$ progeny seed; and
(d) selecting said $F_2$-plants for having *Bremia* resistance, currant-lettuce aphid (*Nasonovia ribis-nigri*) and lettuce mosaic virus (LMV).

* * *

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A lettuce plant designated "79-88 RZ", representative seed of which having been deposited under NCIMB Accession No. 41615, wherein said plant has resistance to downy mildew (*Bremia lactucae* Regal), currant-lettuce aphid (*Nasonovia ribis-nigri*) and lettuce mosaic virus (LMV).

2. A seed of the plant of claim 1.

3. A plant that has all of the morphological and physiological characteristics of lettuce cultivar 79-88 RZ, representative seed of which having been deposited under NCIMB Accession No. 41615, said plant grown from the seed of claim 2.

4. A $F_1$ progeny of the lettuce plant of claim 3.

5. A part of the plant of claim 1, wherein said part of the plant is suitable for sexual reproduction.

6. The part of the plant of claim 5, said part selected from the group consisting of microspores, pollen, ovaries, ovules, embryo sacs and egg cells.

7. A plant that has all of the morphological and physiological characteristics of lettuce cultivar 79-88 RZ, representative seed of which having been deposited under NCIMB Accession No. 41615, said plant regenerated from the part of the plant of claim 5.

8. A $F_1$ progeny of the lettuce plant of claim 7.

9. A part of the plant of claim 1, wherein said part of the plant is suitable for vegetative reproduction.

10. The part of the plant of claim 9, said part selected from the group consisting of cuttings, roots, stems, cells and protoplasts.

11. A tissue culture of regenerable cells or protoplasts from the lettuce plant of claim 1.

12. The tissue culture of claim 11, wherein said cells or protoplasts of the tissue culture which are derived from a tissue selected from the group consisting of leaves, pollen, embryos, cotyledon, hypocotyls, meristematic cells, roots, root tips, anthers, flowers, seeds and stems.

13. A plant that has all of the morphological and physiological characteristics of lettuce cultivar 79-88 RZ, representative seed of which having been deposited under NCIMB Accession No. 41615, said plant regenerated from the tissue culture of claim 11.

14. A $F_1$ progeny of the lettuce plant of claim 13.

15. A $F_1$ progeny of the lettuce plant of claim 1.

16. A $F_1$ progeny of the lettuce plant of claim 1, wherein the plant has the resistance to downy mildew (*Bremia lactucae* Regal), currant-lettuce aphid (*Nasonovia ribis-nigri*) and lettuce mosaic virus (LMV) as found in lettuce cultivar 79-88 RZ, representative seed of which having been deposited under NCIMB Accession No. 41615, and is modified in one or more other characteristics.

17. The progeny of claim 16, wherein the modification is effected by transformation with a transgene.

18. A method of producing a hybrid lettuce seed, comprising: crossing a first parent lettuce plant with a second parent lettuce plant and harvesting the resultant hybrid lettuce seed, wherein said first parent lettuce plant or said second parent lettuce plant is the lettuce plant of claim 1.

19. A $F_1$ progeny of a lettuce plant of claim 1, wherein said progeny is produced by sexual reproduction of said lettuce plant, and wherein the progeny has all of the morphological and physiological characteristics of lettuce cultivar 79-88 RZ, representative seed of which having been deposited under NCIMB Accession No. 41615.

20. A progeny of the lettuce plant of claim 1, wherein said progeny is produced by vegetative reproduction of said lettuce plant or a progeny plant thereof, and wherein the progeny has all of the morphological and physiological characteristics of lettuce cultivar 79-88 RZ, representative seed of which having been deposited under NCIMB Accession No. 41615.

* * * * *